United States Patent
Bouillot et al.

(10) Patent No.: US 12,071,402 B2
(45) Date of Patent: Aug. 27, 2024

(54) IMMUNOSUPPRESSANT FORMULATIONS

(71) Applicant: Novartis AG, Basel (CH)

(72) Inventors: Philippe Michel Rene Bouillot, Basel (CH); Emeric Reynaud, Village Neuf (FR)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 17/230,175

(22) Filed: Apr. 14, 2021

(65) Prior Publication Data

US 2022/0064110 A1 Mar. 3, 2022

Related U.S. Application Data

(63) Continuation of application No. 16/804,926, filed on Feb. 28, 2020, now abandoned, which is a continuation of application No. 13/917,730, filed on Jun. 14, 2013, now abandoned, which is a continuation-in-part of application No. PCT/EP2012/050151, filed on Jan. 5, 2012.

(30) Foreign Application Priority Data

Jan. 7, 2011 (EP) .................................... 11150431

(51) Int. Cl.
*C07D 205/04* (2006.01)
*A61K 9/20* (2006.01)
*A61K 31/397* (2006.01)

(52) U.S. Cl.
CPC .......... *C07D 205/04* (2013.01); *A61K 9/2004* (2013.01); *A61K 31/397* (2013.01)

(58) Field of Classification Search
CPC .......... A61K 31/397; A61K 9/20; A61P 43/00
See application file for complete search history.

(56) References Cited

U.S. PATENT DOCUMENTS

| | | | |
|---|---|---|---|
| 3,872,113 A | 3/1975 | Fliedner, Jr. | |
| 5,604,229 A | 2/1997 | Fujita et al. | |
| 6,121,329 A | 9/2000 | Fujii et al. | |
| 7,288,537 B2 | 10/2007 | Le Grand et al. | |
| 8,492,441 B2 | 7/2013 | Legangneux | |
| 2005/0014728 A1 | 1/2005 | Pan et al. | |
| 2005/0090520 A1 | 4/2005 | Lindquist | |
| 2006/0173052 A1 | 8/2006 | Rundfeldt et al. | |
| 2006/0198884 A1 | 9/2006 | Yang et al. | |
| 2009/0005458 A1 | 1/2009 | Rombout et al. | |
| 2009/036423 A1 | 2/2009 | Gray | |
| 2012/0115840 A1 | 5/2012 | Ciszewski et al. | |

FOREIGN PATENT DOCUMENTS

| | | | |
|---|---|---|---|
| CA | 2521325 A1 | 10/2004 | |
| CN | 103458877 A | 12/2013 | |
| EP | 3047848 A1 | 7/2016 | |
| RU | 2296999 C2 | 4/2007 | |
| WO | 200066116 A2 | 11/2000 | |
| WO | 0218395 A1 | 3/2002 | |
| WO | 03097028 A1 | 11/2003 | |
| WO | 2004103306 A2 | 12/2004 | |
| WO | 2004113330 A1 | 12/2004 | |
| WO | 2005000833 A1 | 1/2005 | |
| WO | 2005044262 A1 | 5/2005 | |
| WO | 2005105146 A1 | 11/2005 | |
| WO | 2006058316 A1 | 6/2006 | |
| WO | 2006094705 A1 | 9/2006 | |
| WO | 2007021666 A2 | 2/2007 | |
| WO | 2007048219 A2 | 5/2007 | |
| WO | 2008000419 A1 | 1/2008 | |
| WO | 2008072056 A1 | 6/2008 | |
| WO | 2008128739 A1 | 10/2008 | |
| WO | 2008135522 A1 | 11/2008 | |
| WO | WO-2009048993 A2 * | 4/2009 | ........... A61K 31/133 |
| WO | 2009115954 A1 | 9/2009 | |
| WO | 2009155475 A1 | 12/2009 | |
| WO | 2010010127 A1 | 1/2010 | |
| WO | 2010020610 A1 | 2/2010 | |
| WO | 2010070083 A1 | 6/2010 | |
| WO | 2010071794 A1 | 6/2010 | |
| WO | 2010072703 A1 | 7/2010 | |
| WO | 2010075239 A1 | 7/2010 | |
| WO | 2010080455 A1 | 7/2010 | |
| WO | WO-2010080409 A1 * | 7/2010 | ........... A61K 31/397 |
| WO | 2012093161 A1 | 7/2012 | |
| WO | 2012095853 A1 | 7/2012 | |
| WO | 2013055833 A1 | 4/2013 | |
| WO | 2014161606 A1 | 10/2014 | |
| WO | 2015155711 A1 | 10/2015 | |

OTHER PUBLICATIONS

Vippagunta, S.R. et al. "Crystalline solids" Advanced Drug Delivery Reviews 2001, 48, 3-26 (Year: 2001).*
Ando, H.Y.; Radebaugh, G.W. "Property-Based Drug Design and Preformulation" Remington: The Science and Practice of Pharmacy, 21st Edition. (2005) Chapter 38. pp. 720-744 (Year: 2005).*
Reilly, W.J. "Pharmaceutical Necessities" Remington: The Science and Practice of Pharmacy, 21st Edition. (2005) chapter 55, pp. 1058-1092 (Year: 2005).*
Ando, H.Y.; Radebaugh, G.W. "Property-Based Drug Design and Preformulation" Remington: The Science and Practice of Pharmacy, 21st Edition. (2005) Chapter 38. pp. 720-744.
Porter, S.C. "Coating of Pharmaceutical Dosage Forms" Remington: The Science and Practice of Pharmacy, 21st Edition. (2005) Chapter 46. pp. 929-938.

(Continued)

*Primary Examiner* — Andrew S Rosenthal
(74) *Attorney, Agent, or Firm* — Adil R. Zhugralin

(57) ABSTRACT

The present invention relates to a solid phase pharmaceutical composition comprising one or more pharmaceutically acceptable excipients and an active pharmaceutical ingredient ("API") which is a compound of formula A1 or A2 or a pharmacologically acceptable salt, solvate or hydrate thereof, wherein the API is not exposed to a basic compound.

12 Claims, 3 Drawing Sheets

(56) References Cited

OTHER PUBLICATIONS

Kalia, J.; Raines, R.T. "Hydrolytic Stability of Hydrazones and Oximes" Agnew. Chem. Int. Ed. Engl. 2008, 47 (39), 7523-7526.
Vippagunta, S.R.; Brittain, H.G.; Grant, D.J.W. "Crystalline solids" Advanced Drug Delivery Reviews 2001, 48, 3-26.
Reilly, W.J. "Pharmaceutical Necessities" Remington: The Science and Practice of Pharmacy, 21st Edition. (2005) Chapter 55. pp. 1058-1092.
Illinois Poison Center (https://illinoispoisioncenter.org/my-child-ate-Silica-Gel) accessed Mar. 24, 2015.
Palmowski, L.M.; Muller, J.A. "Anaerobic degradation of organic materials—significance of the substrate surface area" Water Science & Technology 2003, 47, 12, 231-238.
Zhigang Sun et al., Particle Size Specifications for Solid Oral Dosage Forms: A regulartory Perspective, American Pharmaceutical Review, May 1, 2010 Paragraph 1 on p. 1 to paragraph 1 on p. 2.
Jivraj, M. et al. "An overview of the different excipients useful for the direct compression of tablets" PSTT vol. 3, No. 2 Feb. 2000 (Year:2000).
"Pharmaceutical experimental design", Chapter 5, Gareth A. Lewis, Didier Mathieu, Roger phan-Tan-Luu, 2005.
N.H. Shah, et al. Evaluation of Two New Tablet Lubricants—Sodium Stearyl Fumarate and Glyceryl Behenate. Measurement of Physical Parmeters (Compaction, Ejection and Residual Forces) in the Tableting Process and the Effect on the Dissolution Rate, Drug Development and Industrial Pharmacy, 12:8-9, 1329-1346, DOI: 10.3109/03639048609065862.
Adachi, et al., FTY720 Story. Its Discovery and the Following Accelerated Development of Sphingosine 1-Phosphate Receptor Agonists as Immunomodulators Based on Reverse Pharmacology, Perspectives in Medicinal Chemistry, 1, 11-23, 2007.
Aki, et al., FTY720: a new kid on the block for transplant immunosuppression, Expert Opinion on Biological Therapy, 3(4), 665-681, Mar. 3, 2003.
Bayas, et al., Managing the Adverse Effects of Interferon-β Therapy in Multiple Sclerosis, Drug Safety, 22(2), 149-159, Feb. 2000.
Biswal, et al., Effects of siponimod (BAF312) alone and when combined with propranolol on absolute lymphocyte count decrease and recovery in healthy subjects, European Journal of Neurology, 21(suppl. 1), 452, 2014.
Biswal, et al., Pharmacokinetic and pharmacodynamic interaction of siponimod (BAF312) and propranolol in healthy subjects, International Journal of Clinical Pharmacology and Therapeutics, 53(10), 855-865, 2015.
Boon, et al., Choosing a dosage regimen, Davidson's Principles and Practice of Medicine, 20, 24-25, 2006.
Brinkmann, et al., FTY720: targeting G-protein-coupled receptors for sphingosine 1-phosphate in transplantation and autoimmunity, Current Opinion In Immunology, 14, 569-575, Jul. 19, 2002.
Brinkmann, et al., The Immune Modulator FTY720 Targets Sphingosine 1-Phosphate Receptors, The Journal of Biological Chemistry, 277(24), 21453-21457, Jun. 14, 2002.
Brinkmann, FTY720 (fingolimod) in Multiple Sclerosis: therapeutic effects in the immune and the central nervous system, British Journal of Pharmacology, 158, 1173-1182, 2009.
Brossard, et al., Pharmacokinetics and pharmacodynamics of ponesimod, a selective S1P1 receptor modulator, in the first-in-human study, British Journal of Clinical Pharmacology, 76(6), 888-896, Apr. 18, 2013.
Brown, et al., Fingolimod: A Novel Immunosuppressant for Multiple Sclerosis, The Annals of Pharmacotherapy, 41, 1660-1668, Oct. 2007.
Budde, et al., First Human Trial of FTY72O, a Novel Immunomodulator, in Stable Renal Transplant Patients, Journal of American Society of Nephrology, 13, 1073-1083, 2002.
Bunemannm, et al., A novel membrane receptor with high affinity for lysosphingomyelin and sphingosine 1-phosphate in atrial myocytes, The EMBO Journal, 15(20), 5527-5534, 1996.
Clinical trial NCT00333138, Jun. 2, 2006, available at https://www.clinicaltrials.gov/ct2/show/NCT00333138.
Dijkmans, Safety Aspects of Cyclosporin in Rheumatoid Arthritis, Drugs, 50(suppl. 1), 41-47, 1995.
Fam, et al., Efficacy and Safety of Desensitization to Allopurinol following Cutaneous Reactions, Arthritis and Rheumatism, 44(1), 231-238, Jan. 2001.
Forrest, et al., Immune Cell Regulation and Cardiovascular Effects of Sphingosine 1-Phosphate Receptor Agonists in Rodents Are Mediated via Distinct Receptor Subtypes, Journal of Pharmacology and Experimental Therapeutics, 309(2), 758-768, 2004.
Fowden, Azetidine-2-carboxylic Acid: a New Cyclic Imino Acid Occurring in Plants, Biochemical Journal, 64, 323-332, 1956.
Frohman, et al., Disease-modifying therapy in multiple sclerosis: strategies for optimizing management, The Neurologist, 8(4), 227-236, 2002.
Gamboa, et al., Pneumocystis Carinii Pneumoniae. Complicating Cytotoxic Therapy in Systemic Vasculitis, An. Med. Intern., 12(11), 555-556, 1995.
Goodman, et al., The Pharmacological Basis of Therapeutics, 9, 43-62; 1363-1382, 1996.
Gottlieb, et al., Tolerability of β-blocker initiation and titration in the Metoprolol CR/XL Randomized Intervention Trial in Congestive Heart Failure (MERIT-HF), Circulation, 105, 1182-1188, 2002.
Graler, et al., The Immunosuppressant FTY720 down-regulates sphingosine 1-phosphate G protein-coupled receptors, The FASEB Journal, Jan. 8, 2004.
Guo, et al., Effects of sphingosine 1-phosphate on pacemaker activity in rabbit sino-atrial node cells, Pflügers Arch—Eur J Physiol, 438, 642-648, Jun. 22, 1999.
Horn, et al., Get to Know an Enzyme: CYP2C9, Pharmacy Times, Mar. 1, 2008.
Dong-Soon Im et al., Molecular Cloning and Characterization of a Lysophosphatidic Acid Receptor, Edg-7, Expressed in Prostate, Molecular Pharmacology, 57, 753-759, 2000.
Kappos, et al., Oral Fingolimod (FTY720) for Relapsing Multiple Sclerosis, N Eng J Med., 355, 1124-1140, Sep. 14, 2006.
Kappos, et al., Siponimod (BAF312) for the Treatment of Secondary Progressive Multiple Sclerosis: Design of the Phase 3 EXPAND Trial, Neurology, 2013.
Kappos, et al., Siponimod (BAF312) for the Treatment of Secondary Progressive Multiple Sclerosis: Design of the Phase 3 EXPAND Trial, Neurology, 80, 2013.
Kerr, Phase I clinical trials: Adapting methodology to face new challenges, Annals of Oncology, 5(suppl. 4), S67-S70, 1994.
Kinshuck, Blood pressure and diabetes Dec. 2009, Medweb, Dec. 2009.
Kirchheiner, et al., Clinical implications of pharmacogenetics of cytochrome P450 drug metabolizing enzymes, Biochimica et Biophysica Acta, 1770, 489-494, 2007.
Koch-Weser, The Serum Level Approach to Individualization of Drug Dosage, European Journal of Clinical Pharmacology, 9, 1-8, 1975.
Kondratyeva, Technology of Dosage Forms, M.Medicine, 1, 1991.
Kovarik, et al., The ability of atropine to prevent and reverse the negative chronotropic effect of fingolimod in healthy subjects, British Journal of Clinical Pharmacology, 66(2), 199-206, May 27, 2008.
Koyrakh, et al., The Heart Rate Decrease C Administration Is Mediated Potassium Channel IKACh, American Journal of Transplantation, 5, 529-536, Jan. 21, 2005.
Kremenchutzky, et al., The safety and efficacy of IFN-beta products for the treatment of multiple sclerosis, Expert Opinion on Drug Safety, 6(3), 279-288, May 4, 2007.
Kukin, β-Blockers in Chronic Heart Failure: Considerations for Selecting an Agent, Mayo Clin Proc., 77, 1199-1206, 2002.
Langer-Gould, et al., Strategies for managing the side effects of treatments for multiple sclerosis, Neurology, 63 (suppl. 5), S35-S41, 2004.
Legangneux, et al., Dose titration of BAF312 attenuates the initial heart rate reducing effect in healthy subjects, British Journal of Clinical Pharmacology, 75(3), 831-841, 2013.
Mehling, et al., FTY720 therapy exerts differential effects on T cell subsets in multiple sclerosis, Neurology, 71, 1261-1267, Oct. 14, 2008.

(56) References Cited

OTHER PUBLICATIONS

Metelitsa, Side effects of drugs, Guide to Clinical Pharmacology of cardiovascular drugs, 37, 1996.
Min, et al., Complications Associated with Immunosuppressive Therapy and Their Management, Pharmacotherapy, 11(5), 119S-125S, 1991.
Multiple Sclerosis Counseling Points, Immunosuppressive Therapy: What you need to know, A Roundtable Discussion, vol. 3, No. 1, Apr. 2007.
Munschauer, et al., Managing Side Effects of Interferon-Beta in Patients with Relapsing-Remitting Multiple Sclerosis, Clinical Therapeutics, 19(5), 883-893, 1997.
Peters, et al., Sphingosine-1-phosphate signaling in the cardiovascular system, Current Opinion in Pharmacology, 7, 186-192, Feb. 5, 2007.
Ramanuja, et al., Approach to "Aspirin Allergy" in Cardiovascular Patients, Circulation, 110, e1-e4, 2004.
Rettie, et al., Clinical and Toxicological Relevance of CYP2C9: Drug-Drug Interactions and Pharmacogenetics, Annu. Rev. Pharmacol. Toxicol., 45, 477-494, 2005.
Rohatagi, et al., Use of an Exposure-Response Model to Aid Early Drug Development of an Oral Sphingosine 1-Phosphate Receptor Modulator, J Clin Pharmacol, 49, 50-62, 2009.
Rovaris, et al., Secondary progressive multiple sclerosis: current knowledge and future challenges, The Lancet Neurolgy, 5, 343-354, Apr. 2006.
Sanna, et al., Sphingosine 1-Phosphate (S1P) Receptor Subtypes S1P1 and S1P3, Respectively, Regulate Lymphocyte Recirculation and Heart Rate, The Journal of Biological Chemistry, 279(14), 13839-13848, Apr. 2, 2004.
Saruwatari, et al., Pharmacogenomics—Basic research on drug therapy. Genetic Polymorphisms of Drug-Metabolizing Enzymes and EM/PM, Nippon Rinsho, 60(1), 58-63.
Schmouder, et al., FTY720 multiple dosing does not result in progressive reduction of heart rate, American Journal of Transplantation, abstract 950, 398, 2005.
Schmouder, et al., FTY720: Placebo-Controlled Study of the Effect on Cardiac Rate and Rhythm in Healthy Subjects, Journal of Clinical Pharmacology, 46, 895-904, 2006.
Schmouder, et al., Oral fingolimod (FTY720), 0.5 or 1.25 mg, for 14 days has no effect on cardiac function, Multiple Sclerosis, 14, S177, P507, 2008.
Selmaj, et al., Siponimod for patients with relapsing-remitting multiple sclerosis (Bold): an adaptive, dose-ranging, randomised, phase 2 study, Lancet Neurology, 12, 756-767, Aug. 2013.
Slade, et al., FTY720 heart rate reduction: doses from 5 mg to 40mg do not result in any greater heart rate effect, American Journal of Transplantation, abstract 952, 398, 2005.
Suarez-Kurtz, Pharmacogenomics in admixed populations, Trends in Pharmacological Sciences, 26(4), 196-201, Apr. 2005.
Sugiyama, et al., Effects of Sphingosine I-Phosphate, a Naturally Occurring Biologically Active Lysophospholipid, on the Rat Cardiovascular System, Japanese Journal of Pharmacology, 82, 338-342, 2000.
Sune Negre, New Galenic Developments to Forms of Administration, 30-65.
Takahashi, Lipid Mediator Sphingosine-1-Phosphate (SIP): Efficacy of Novel SIP Receptor Agonists in the Treatment of Autoimmune Diseases, Shinshu Medical Journal, 57(4), 127-136, 2009.
Therapeutics Letter, Oct. 1995, Therapeutics Initiative: Evidence based drug therapy, Dose Titration: Minimize to Maximize.
Tranchand, Methodologie des essais cliniques en cancerologie, La Lettre du Pharmacologue, 22(3), 98-110, Jul.-Aug.-Sep. 2008.
Wikipedia, Medicamento, Jul. 26, 2011.
Wroe, Effects of Dose Titration on Tolerability and Efficacy of Interferon Beta-1b in People with Multiple Sclerosis, The Journal of International Medical Research, 33, 309-318, 2005.
NCT00879658.
NCT00422175.
NCT01185821.
NCT01565902.
NCT01904214.
NCT01665144.

* cited by examiner

IMMUNOSUPPRESSANT FORMULATIONS

RELATED APPLICATIONS

This application is a continuation of U.S. application Ser. No. 16/804,926, filed on Feb. 28, 2020, which is a continuation of U.S. application Ser. No. 13/917,730, filed on Jun. 14, 2013, which is a continuation-in-part of International Patent Application No. PCT/EP2012/050151, which claims the benefit of the filing date of European Patent Application No. 11150431.2, filed Jan. 7, 2011, the entire contents of each of which are incorporated herein by reference in their entireties.

FIELD OF THE INVENTION

The present invention relates to formulations of immunosuppressant compounds, and particularly to formulations of S1P receptor modulators. More particularly the invention relates to formulations of 1-{4-[1-(4-cyclohexyl-3-trifluoromethyl-benzyloxyimino)-ethyl]-2-ethyl-benzyl}-azetidine-3-carboxylic acid, pharmaceutically acceptable salts, and related compounds.

BACKGROUND TO THE INVENTION

S1P receptors belong to a family of closely related, lipid activated G-protein coupled receptors. S1P1, S1P3, S1P2, S1P4, and S1P5 (also respectively termed EDG-1, EDG-3, EDG-5, EDG-6, and EDG-8) are identified as receptors specific for sphingosine-1-phosphate (S1P). Certain S1P receptors are associated with diseases mediated by lymphocyte interactions, for example, in transplantation rejection, autoimmune disease, inflammatory diseases, infectious diseases and cancer.

WO2004/103306 discloses immunosuppressant compounds that are useful in the treatment of diseases associated with S1P receptor mediated signal transduction. The immunosuppressant compounds disclosed in WO2004/103306 affect the pathology and/or symptomology of these diseases by altering the activity of S1P receptors. In particular, WO2004/103306 and US 2009/0036423 disclose 1-{4-[1-(4-cyclohexyl-3-trifluoromethyl-benzyloxyimino)-ethyl]-2-ethyl-benzyl}-azetidine-3-carboxylic acid:

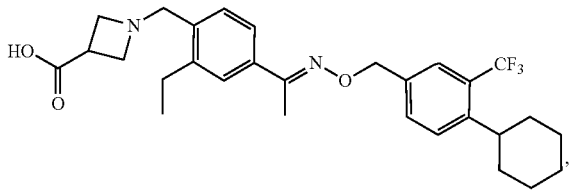 [SMILES: CCc1cc(/C(C)=N/OCC2=CC=C(C3CCCCC3)C(C(F)(F)F)=CC2)ccc1CN1CC(C(=O)O)C1]

and methods for making this compound. The compounds are disclosed as useful in the treatment and/or prevention of diseases and disorders mediated by lymphocyte interactions, for example autoimmune diseases, e.g. rheumatoid arthritis, systemic lupus erythematosus, Hashimoto's thyroiditis and multiple sclerosis, amongst many others. WO2004/103306 and US 2009/0036423 are incorporated herein by reference for all purposes, including by way of non-limiting example paragraphs [0041]-[0054], inclusive, of US 2009/0036423 and each example thereof.

WO2010/020610 discloses use of S1P receptor agonists, for example 1-{4-[1-(4-cyclohexyl-3-trifluoromethyl-benzyloxyimino)-ethyl]-2-ethyl-benzyl}-azetidine-3-carboxylic acid, in the treatment of peripheral neurapathies, such as Guillain-Barre syndrome (GBS), chronic inflammatory demyelinating polyradiculoneuropathy (CIDP), multifocal motor neuropathy with conduction block (MMN), and paraproteinaemic demyelinating peripheral neuropathy (PDN).

WO2007/021666 discloses a concentrate for dilution comprising a S1P receptor agonist, propylene glycol and optionally glycerin, which concentrate is described as being stable for extended periods of time. One compound mentioned as an S1P receptor agonist is 1-{4-[1-(4-cyclohexyl-3-trifluoromethyl-benzyloxyimino)-ethyl]-2-ethyl-benzyl}-azetidine-3-carboxylic acid. The dilution disclosed in WO2007/021666 is provided in a liquid form and is therefore particularly suitable for patients who struggle to swallow solid medications.

WO2009/048993 discloses compositions comprising S1P receptor modulators, such as 2-substituted 2-amino-propane-1,3-diol or 2-amino-propanol derivatives, which are suitable for use as an oral dosage form. The composition is disclosed to comprise the active ingredient and one or more of various specified excipients. Example 10 mentions glyceryl behenate as a non-feasible excipient, seemingly because of degradation of the active (FTY720). One S1P modulator mentioned is 1-{4-[1-(4-cyclohexyl-3-trifluoromethyl-benzyloxyimino)-ethyl]-2-ethyl-benzyl}-azetidine-3-carboxylic acid.

WO2010/072703 discloses a dosage regimen of an S1P receptor modulator for the treatment of patients suffering from an autoimmune disease, for example multiple sclerosis. The dosage regimen comprises administering a lower dosage of an S1P receptor modulator during the initial days of treatment compared to the standard daily dosage. The dosage is then increased stepwise up to the standard daily dosage of the S1P receptor modulator. One S1P modulator mentioned is 1-{4-[1-(4-cyclohexyl-3-trifluoromethyl-benzyloxyimino)-ethyl]-2-ethyl-benzyl}-azetidine-3-carboxylic acid.

SUMMARY OF THE INVENTION

The present invention is predicated at least in part on a finding that, in relation to active pharmaceutical ingredients described later in this specification, pharmaceutical compositions having particular excipients are associated with reduced degradation of the active pharmaceutical ingredient as compared to alternative compositions of the same active pharmaceutical ingredient.

The invention is also predicated at least in part by a finding that provision of the active pharmaceutical ingredient as particles of relatively large size can improve stability whilst maintaining an adequately homogeneous content uniformity.

The compounds to which the application relates are compounds as disclosed in WO 04/103306 and US 2009/0036423, in particular compounds of formula A1 or A2:

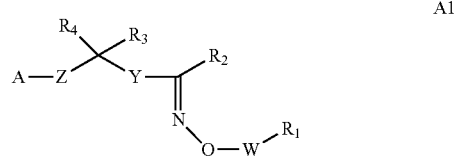

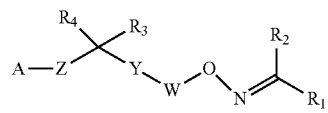

wherein
A is COOR$_5$, OPO(OR$_5$)$_2$, PO(OR$_5$)$_2$, SO$_2$OR$_5$, POR$_5$OR$_5$ or 1H-tetrazol-5-yl, R$_5$ being H or an ester-forming group, e.g. C$_{1-6}$alkyl, and in one implementation of the invention being H;

W is a bond, C$_{1-3}$alkylene or C$_{2-3}$alkenylene;

Y is C$_{6-10}$aryl or C$_{3-9}$heteroaryl, optionally substituted by 1 to 3 radicals selected from halogen, NO$_2$, C$_{1-6}$alkyl, C$_{1-6}$alkoxy; halo-substituted C$_{1-6}$alkyl and halo-substituted C$_{1-6}$alkoxy;

Z is chosen from:

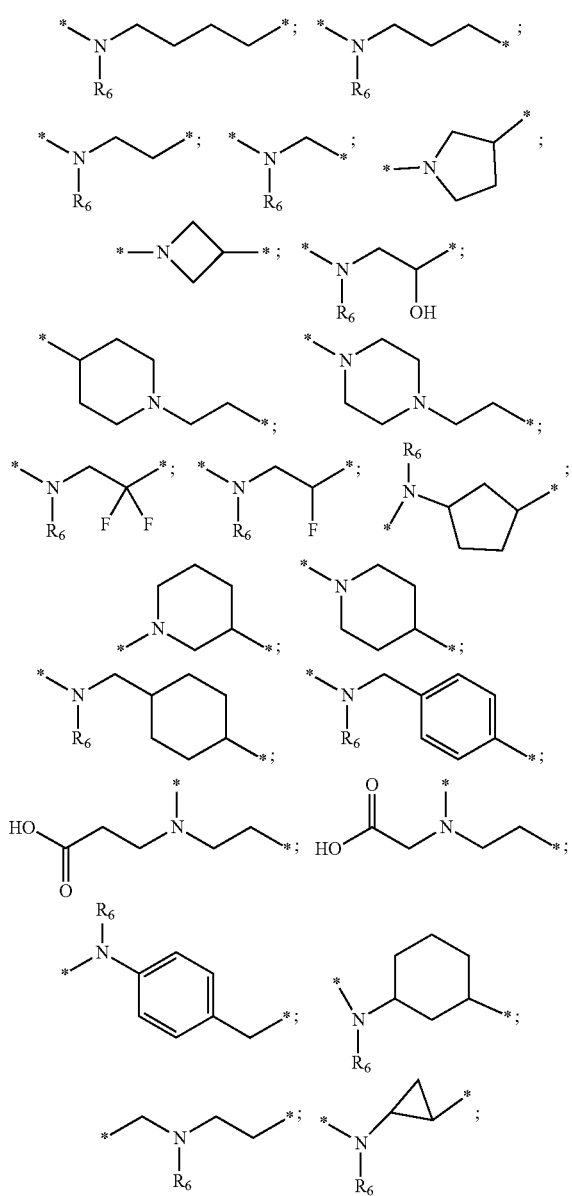

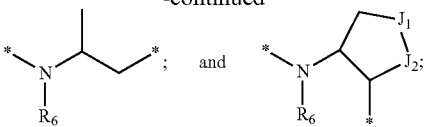

wherein the asterisks of Z indicate the point of attachment between —C(R$_3$)(R$_4$)— and A of Formula Ia or Ib, respectively; R$_6$ is chosen from hydrogen and C$_{1-6}$alkyl; and J$_1$ and J$_2$ are independently methylene or a heteroatom chosen from S, O and NR$_5$; wherein R$_5$ is chosen from hydrogen and C$_{1-6}$alkyl; and any alkylene of Z can be further substituted by one to three radicals chosen from halo, hydroxy, C$_{1-6}$alkyl; or R$_6$ can be attached to a carbon atom of Y to form a 5-7 member ring;

R$_1$ is C$_{6-10}$aryl or C$_{3-9}$heteroaryl, optionally substituted by C$_{1-6}$alkyl, C$_{6-10}$aryl, C$_{6-10}$arylC$_{1-4}$alkyl, C$_{3-9}$heteroaryl, C$_{3-9}$heteroarylC$_{1-4}$alkyl, C$_{3-8}$cycloalkyl, C$_{3-8}$cycloalkylC$_{1-4}$alkyl, C$_{3-8}$heterocycloalkyl or C$_{3-8}$heterocycloalkylC$_{1-4}$alkyl; wherein any aryl, heteroaryl, cycloalkyl or heterocycloalkyl of R$_1$ may be substituted by 1 to 5 groups selected from halogen, C$_{1-6}$alkyl, C$_{1-6}$alkoxy and halo substituted-C$_{1-6}$alkyl or —C$_{1-6}$alkoxy;

R$_2$ is H, C$_{1-6}$alkyl, halo substituted C$_{1-6}$alkyl, C$_{2-6}$alkenyl or C$_{2-6}$alkynyl; and each of R$_3$ or R$_4$, independently, is H, halogen, OH, C$_{1-6}$alkyl, C$_{1-6}$alkoxy or halo substituted C$_{1-6}$alkyl or C$_{1-6}$alkoxy;

or a pharmacologically acceptable salt, solvate or hydrate thereof.

In the above formula, the designation "C$_{1-6}$" means "having 1, 2, 3, 4, 5 or 6 carbon atoms" and the designation "C$_{3-6}$" means "having 3, 4, 5, 6, 7 or 8 carbon atoms". The designation "C$_{1-4}$" means "having 1, 2, 3 or 4 carbon atoms". The designation "C$_{3-9}$" means "having 3, 4, 5, 6, 7, 8 or 9 carbon atoms".

The invention particularly, but not exclusively, involves compounds of formula A1 or A2 in which R$_5$ is H, e.g. moiety A is —COOH, in its acid form (not therefore as a salt thereof).

An exemplary compound of formula A1 or A2 is 1-{4-[1-(4-cyclohexyl-3-trifluoromethyl-benzyloxyimino)-ethyl]-2-ethyl-benzyl}-azetidine-3-carboxylic acid and its pharmaceutically acceptable salts, e.g. its hemifumarate salt.

In one aspect, the invention provides a pharmaceutical composition comprising an active pharmaceutical ingredient ("API") selected from the compounds of Formulae A1 and A2, and one or more pharmaceutically acceptable excipients, wherein the API is not exposed to a basic compound.

In another aspect, the invention provides a pharmaceutical composition comprising an active pharmaceutical ingredient ("API") selected from the compounds of Formulae A1 and A2, wherein the API is in the form of particles having an X90 diameter of at least 8 μm and optionally of at least 10 μm.

The invention also provides a pharmaceutical composition comprising an active pharmaceutical ingredient ("API") selected from the compounds of Formulae A1 and A2, wherein the API is in the form of particles having a crystallinity of 80% or more.

Further included in the invention are pharmaceutical compositions comprising an active pharmaceutical ingredient ("API") selected from the compounds of Formulae A1 and A2, wherein the API is in the form of particles having an X90 diameter of at least 8 μm and optionally of at least 10 μm and a crystallinity of 80% or more.

The invention includes a pharmaceutical composition comprising an active pharmaceutical ingredient ("API") selected from the compounds of Formulae A1 and A2, and one or more pharmaceutically acceptable excipients, wherein the API is in the form of particles which have an X90 diameter of at least 8 μm and optionally of at least 10 μm and which are not exposed to a basic compound. In an embodiment, the composition is free of basic compounds.

The invention includes pharmaceutical compositions comprising an active pharmaceutical ingredient ("API") selected from the compounds of Formulae A1 and A2, and one or more pharmaceutically acceptable excipients, wherein the API is in the form of particles which have a crystallinity of 80% or more and which are not exposed to a basic compound.

Additionally to be mentioned as provided by the invention are pharmaceutical compositions comprising an active pharmaceutical ingredient ("API") selected from the compounds of Formulae A1 and A2, and one or more pharmaceutically acceptable excipients, wherein the API is in the form of particles which have an X90 diameter of at least 8 μm and optionally of at least 10 μm and a crystallinity of 80% or more and which are not exposed to a basic compound.

The composition is in particular a solid phase composition, for example a tablet or capsule, particularly a tablet. The composition may be coated with a moisture barrier and an exemplary composition is a tablet coated with a moisture barrier.

The pharmaceutical composition may therefore comprise, or consist of, at least one API and one or more non-basic excipients. The one or more non-basic excipients may be selected from binders, disintegrants, glidants, lubricants, fillers, diluents, and/or sorbents. The tablets may comprise one or more tablet lubricants wherein the lubricants in the tablets are selected exclusively from stearic acid, hydrogenated vegetable oil, mineral oil, polyethylene glycol 4000-6000, gyceryl palmitostearate and glyceryl behenate.

In one embodiment, the pharmaceutical composition comprises a non-basic sustained release agent, for example a non-basic hydrogel former, e.g. a hypromellose (hydroxypropylmethyl cellulose).

A particular embodiment resides in a tablet comprising a compressed mixture which consists of 1-{4-[1-(4-cyclohexyl-3-trifluoromethyl-benzyloxyimino)-ethyl]-2-ethyl-benzyl}-azetidine-3-carboxylic acid or a pharmaceutically acceptable salt thereof e.g. a hemifumarate salt and one or more non-basic excipients. The 1-{4-[1-(4-cyclohexyl-3-trifluoromethyl-benzyloxyimino)-ethyl]-2-ethyl-benzyl}-azetidine-3-carboxylic acid or salt in a particular implementation is in the form of particles which have an X90 diameter of from 10 μm to 200 μm and/or which are at least 80% crystalline. The compressed mixture may include a desiccant and/or be coated with a moisture barrier (e.g. both includes a desiccant and have a moisture barrier coating).

The pharmaceutical compositions of the present invention may be used to treat autoimmune diseases, e.g. rheumatoid arthritis, systemic lupus erythematosus, Hashimoto's thyroiditis and multiple sclerosis, amongst many others, e.g. as disclosed in WO2004/103306 and US 2009/0036423 for example in paragraphs [0041]-[0042] of US 2009/0036423. The pharmaceutical compositions of the present invention may be used to treat peripheral neuropathies, for example motor neuron disease, Guillain-Barre syndrome (GBS), chronic inflammatory demyelinating polyradiculoneuropathy (CIDP), multifocal motor neuropathy with conduction block (MMN), or paraproteinaemic demyelinating peripheral neuropathy (PDN). In particular embodiments, the compositions of the invention are used to treat multiple sclerosis. The invention therefore includes a method for treating a subject in need thereof, e.g. having or suspected of having one of the aforesaid diseases, e.g. multiple sclerosis, comprising administering to the patient a composition of the invention. The composition is desirably administered in an effective amount. Also disclosed are compositions of the invention for use in treating at least one of the aforesaid diseases, e.g. multiple sclerosis.

DETAILED DESCRIPTION OF THE INVENTION

Figure 1:
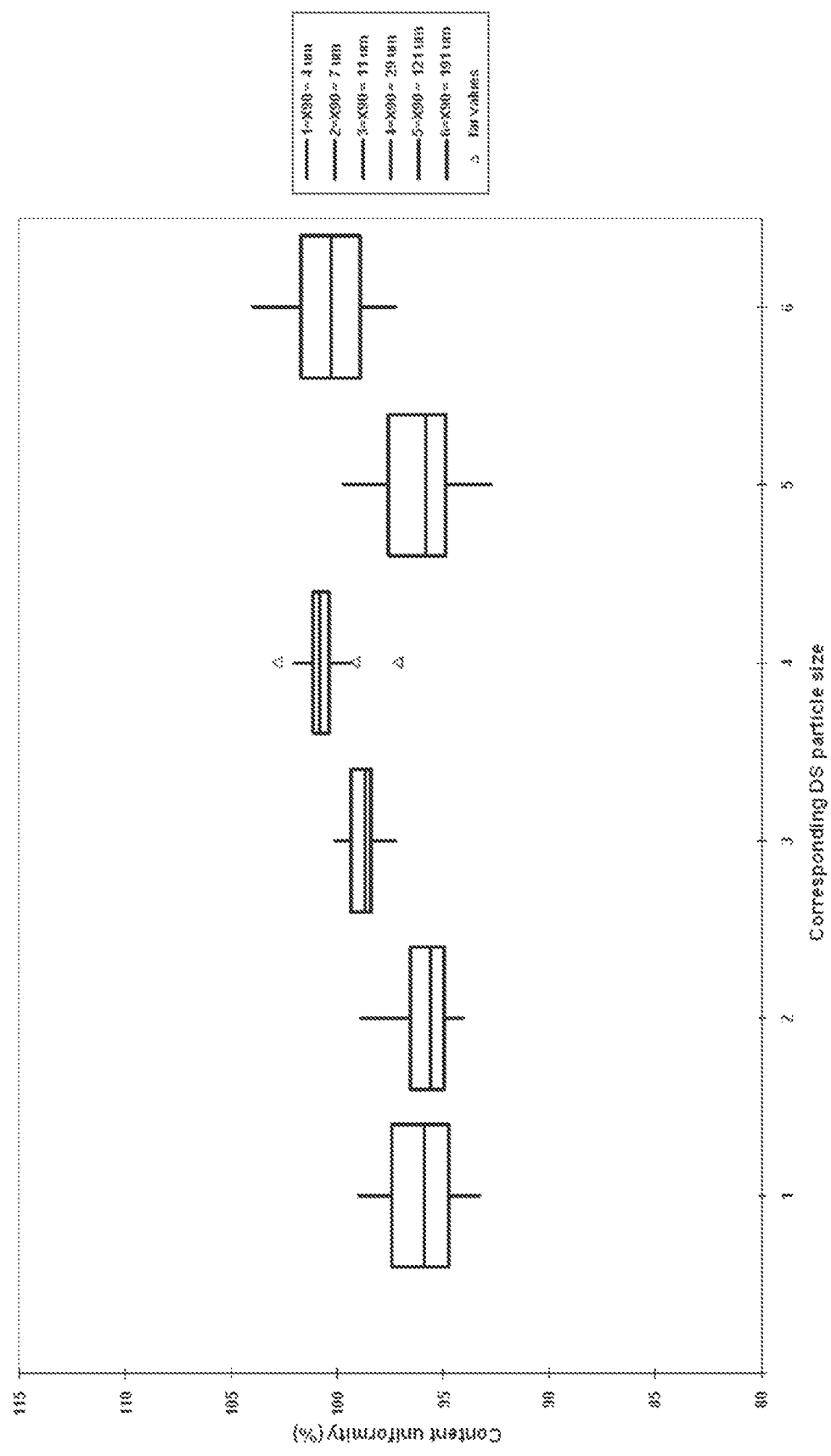
FIG. 1 is a box plot which demonstrates the effect of drug particle size on the content uniformity of a tablet comprising 5 mg (equivalent base weight) of the hemifumarate salt of 1-{4-[1-(4-cyclohexyl-3-trifluoromethyl-benzyloxyimino)-ethyl]-2-ethyl-benzyl}-azetidine-3-carboxylic acid.

For the avoidance of doubt, it is hereby stated that the information disclosed earlier in this specification under the heading "Background to the Invention" is relevant to the invention and is to be read as part of the disclosure of the invention.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification (which term encompasses both the description and the claims) is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "treat" includes: (1) preventing or delaying the appearance of clinical symptoms of the state, disorder or condition developing in an animal, particularly a mammal and especially a human, that may be afflicted with or predisposed to the state, disorder or condition but does not yet experience or display clinical or subclinical symptoms of the state, disorder or condition; (2) inhibiting the state, disorder or condition (e.g., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

"Effective amount" means an amount of an API or pharmaceutical composition sufficient to result in the desired therapeutic response. The therapeutic response can be any response that a user (e.g., a clinician or patient) will recognize as an effective response to the therapy.

The invention relates to oral pharmaceutical compositions comprising as an API an S1P receptor modulator or agonist, e.g. a compound of formula A1 or A2 as defined above. The disclosure describes solid phase dosage units, which may be a tablet or capsule, particularly a tablet. Exemplary compositions, e.g. tablets, contain 10 mg or less of the API (equivalent base weight), e.g. 7.5 mg or less of the API, for example 5 mg or less of the API. Some solid phase dosage units, e.g. tablets, contain 0.1 mg or more API (equivalent base weight), e.g. 0.2 mg or more of the API, for example 0.25 mg or more API. There are therefore included in the invention dosage units, e.g. tablets, which contain from 0.1 mg to 10 mg of the API (equivalent base weight), e.g. 0.2 mg to 7.5 mg of the API; particular dosage units, e.g. tablets, contain from 0.25 mg to 5 mg of the API (equivalent base weight), for example 2.5 mg to 5 mg of the API.

In one implementation of the invention, the dosage units (e.g. tablets) contain no more than 4 mg of the API (equivalent base weight), e.g. from 0.2 mg or 0.25 mg to 4 mg of the API. Some dosage units contain from 2 mg or 2.5 mg to 4 mg of the API (equivalent base weight).

In one embodiment, the dosage units (e.g. tablets) contain 4 mg of the API. In one embodiment, the dosage units (e.g. tablets) mentioned in this paragraph comprise, or consist of, a solid phase mixture consisting of API and non-basic excipients which comprise a cellulosic excipient, e.g. selected from microcrystalline cellulose, hypromellose, ethylcellulose and combinations thereof. In another embodiment, the dosage units (e.g. tablets) mentioned in this paragraph comprise, or consist of, a solid phase mixture consisting of API and non-basic excipients which comprise a controlled release material, e.g. a non-basic hydrogel-former such as, for example, hypromellose. The solid phase mixture may have at least one coating.

In one embodiment, the compound is of formula A1. It will be understood that this embodiment, like all embodiments mentioned herein, is applicable across the entire scope of the disclosure, including to all other embodiments disclosed herein, including those disclosed in the following paragraphs.

In one embodiment, $R_5$ is H.

In one embodiment, A is $COOR_5$, and in particular is COOH.

In one embodiment, Z is

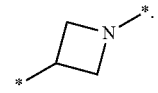

In one embodiment, A-Z is

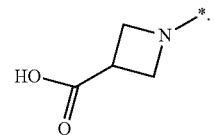

In one embodiment, Y is phenyl optionally substituted by 1, 2 or 3 radicals selected from halogen, $NO_2$, $C_{1-6}$alkyl, $C_{1-6}$alkoxy; halo-substituted $C_{1-6}$alkyl and halo-substituted $C_{1-6}$alkoxy, and in particular Y is phenyl substituted by a single said radical, e.g. by a single $C_{1-6}$ alkyl radical. The designation "$C_{1-6}$" means "having 1, 2, 3, 4, 5 or 6 carbon atoms" and an exemplary $C_{1-6}$ alkyl radical is ethyl.

In one embodiment, A-Z—$C(R_4)(R_3)$—Y— is

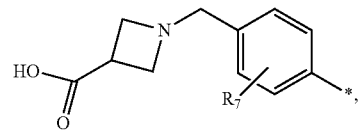

where $R_7$ is H, halogen, $NO_2$, $C_{1-6}$alkyl, $C_{1-6}$alkoxy; halo-substituted $C_{1-6}$alkyl and halo-substituted $C_{1-6}$alkoxy, and in particular is $C_{1-6}$alkyl e.g. ethyl.

In one embodiment, W is $C_1$, $C_2$ or $C_3$ alkylene, particularly methylene. Since every embodiment disclosed herein is applicable to the entire disclosure of the invention, it will be understood that in this case (where W is $C_1$, $C_2$ or $C_3$ alkylene, particularly methylene), the compound may be of the formula A1 and/or Y may be an optionally substituted phenyl group as previously described herein and in particular where A-Z—$C(R_4)(R_3)$—Y— may be

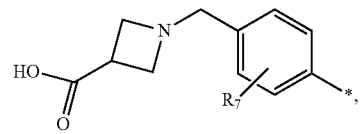

In one embodiment (for example applicable to the embodiments mentioned in the immediately preceding paragraph), $R_1$ is phenyl substituted by phenyl or by $C_3$-$C_8$ cycloalkyl, e.g. by cyclohexyl, wherein each phenyl and cyclohexyl are each independently optionally substituted by 1 or 2 substituents selected from halogen, $C_{1-6}$alkyl, $C_{1-6}$alkoxy and halo substituted-$C_{1-6}$alkyl or —$C_{1-6}$alkoxy. $R_1$ may therefore be phenyl substituted by $C_3$-$C_8$ cycloalkyl, each optionally substituted as just mentioned; in one sub-embodiment, phenyl of $R_1$ is substituted by a single substituent, e.g. fluoro or in particular trifluoromethyl, and cycloalkyl of $R_1$ is unsubstituted cyclohexyl. In an embodiment where the compound is of formula A1, phenyl is 1,4-substituted by W and cycloalkyl (e.g. unsubstituted cyclohexyl). The designation "$C_3$-$C_8$" means having 3, 4, 5, 6, 7 or 8 carbon atoms, e.g. 5 or 6 carbon atoms.

In one embodiment, the compound is of formula A1; W is $C_1$, $C_2$ or $C_3$ alkylene; Y is a phenyl group optionally substituted by 1, 2 or 3 radicals selected from halogen, $NO_2$, $C_{1-6}$alkyl, $C_{1-6}$alkoxy; halo-substituted $C_{1-6}$alkyl and halo-substituted $C_{1-6}$alkoxy; and $R_1$ is phenyl substituted by $C_3$-$C_8$ cycloalkyl, wherein phenyl and cyclohexyl are each independently optionally substituted by 1 or 2 substituents selected from halogen, $C_{1-6}$alkyl, $C_{1-6}$alkoxy and halo substituted-$C_{1-6}$alkyl or —$C_{1-6}$alkoxy.

Pharmaceutical Compositions

The invention in its various aspects is in part predicated on a finding that an active compound as disclosed above, namely the hemifumarate salt of 1-{4-[1-(4-cyclohexyl-3-trifluoromethyl-benzyloxyimino)-ethyl]-2-ethyl-benzyl}-azetidine-3-carboxylic acid, has poor stability in certain settings and that stability of the compound in a pharmaceutical composition may be improved by adopting one, two or three of the following measures:

not exposing the active compound to a basic compound, e.g. excluding basic compounds from the composition (other than the active compound itself when in basic form)

having the active compound in the form of particles having a crystallinity of 80% or more having the active compound in the form of particles having an X90 diameter of at least 8 μm, e.g. at least 10 μm.

It will be appreciated that the hemifumarate salt of 1-{4-[1-(4-cyclohexyl-3-trifluoromethyl-benzyloxyimino)-ethyl]-2-ethyl-benzyl}-azetidine-3-carboxylic acid is a representative of the compounds of formula A1 or A2 as described above and that the just-mentioned measures may therefore be beneficially applied to any such compound as an active pharmaceutical ingredient (API) of a composition.

Advantageously, the composition is substantially dry, e.g. is made of substantially moisture-free constituent, and is provided with a moisture-protective layer as a barrier to ingress of water and/or includes a desiccant.

In one implementation of the invention, the composition, for example in the form of a tablet, comprises a desiccant. In another implementation of the invention, the composition, for example in the form of a tablet, is provided with a moisture-protective layer. In a particular implementation, the composition, for example in the form of a tablet, comprises a desiccant and is provided with a moisture-protective layer.

It is advantageous to combine two or more of the above measures. For example embodiments of the invention lie in solid phase compositions, for examples capsules or tablets, particularly tablets, having one the following characteristics (1) to (6):

(1) the API is not exposed to basic compounds, e.g. basic compounds are excluded from the composition, and the API is in the form of particles having a crystallinity of 80% or more;

(2) the API is not exposed to basic compounds, e.g. basic compounds are excluded from the composition, and the API is in the form of particles having an X90 diameter of at least 8 μm e.g. at least 10 μm;

(3) the API is in the form of particles having an X90 diameter of at least 8 μm e.g. at least 10 μm and a crystallinity of 80% or more;

(4) the API is not exposed to basic compounds, e.g. basic compounds are excluded from the composition, and the API is in the form of particles having an X90 diameter of at least 8 μm e.g. at least 10 μm and a crystallinity of 80% or more;

(5) any of (1), (2), (3) and (4) in combination with inclusion of a desiccant in the composition;

(6) any of (1), (2), (3), (4) and (5) in combination with provision of a moisture-protective layer or coating.

In particular, the above-mentioned APIs have poor stability in admixture with one or more of the following compounds; sodium starch glycolate (sold under the trade mark Primojel®), sodium lauryl sulfate, magnesium stearate, calcium stearate, calcium carbonate, calcium sulfate, sodium stearyl fumarate and sodium bicarbonate. The above-mentioned APIs also have poor stability in admixture with gelatin.

Not exposing the active compound to a basic compound may be achieved by not having the active compound in admixture with a basic compound. In an embodiment, therefore, the API is in a mixture of materials which is free of basic compounds. Conveniently, therefore, the composition is free of basic compounds. However, the invention includes, for example, the provision of two- or multi-part compositions of which one part incorporates a compound of formula A1 or A2 but is free of any basic compound and a second part does not incorporate a compound of formula A1 or A2 but does incorporate a basic compound. It will be understood that the expression "free of any basic compound" and similar expressions do not mean that no base may be present in the composition but does allow very low amounts of base to be present, such an amount therefore being at a concentration which does not for practical purposes promote degradation of the API. For example, a basic compound may be an impurity which it is not possible or practicable to remove entirely or to an undetectable level.

In embodiments, moiety A is not in the form of a salt but $R_5$ is present as H or an ester-forming group. $R_5$ particularly is present as H (i.e. moiety A is in its acid form and not as a salt).

In one embodiment the pharmaceutical composition comprises a solid phase mixture, which may be in the form of a tablet, and which consists of a compound of formula A1 or A2 in admixture with one or more non-basic compounds. The one or more non-basic compounds may comprise or consist of non-basic excipients, e.g. selected from: binders, disintegrants, glidants, lubricants, fillers, diluents, controlled release agents and sorbents. The composition, e.g. tablet, may have one or more coating layers and/or may have an basic component separated from said solid phase mixture by a barrier. Said solid phase mixture may comprise one or more non-basic APIs in addition to one or more APIs of formula A1 or A2. The composition, e.g. tablet, may have a coating layer which is a moisture barrier, for example as sold under the trade mark Opadry® amb. A moisture barrier film composition is described in WO1996/001874, included herein by reference for all purposes, and comprises polyvinyl alcohol, soya lecithin, and optionally a flow aid, a colorant, and/or a suspending agent. Conveniently, the composition includes a desiccant, e.g. colloidal silica.

In one embodiment the pharmaceutical composition comprises a solid phase mixture, which may be in the form of a tablet, and which consists of a compound of formula A1 or A2 in admixture with excipients selected from lactose (e.g. as lactose monohydrate); microcrystalline cellulose; non-basic polymers e.g. homopolymers of cross-linked N-vinyl-2-pyrrolidone (crospovidone), hypromellose (hydroxypropylmethyl cellulose), and ethyl cellulose; waxes; colloidal silicon dioxide; stearic acid; hydrogenated vegetable oil; mineral oil; polyethylene glycol (e.g. polyethylene glycol 4000-6000); gyceryl palmitostearate; and glyceryl behenate. In such a formulation, lactose is considered to act as a filler, microcrystalline cellulose as a binder, crospovidone as a disintegrant, hypromellose and ethyl cellulose as a controlled release agent, colloidal silicon dioxide as a glidant and the remaining materials as lubricants; in embodiments, only a single such lubricant is included in the composition, e.g. glyceryl behenate. Colloidal silicon dioxide acts also as a desiccant. Hydrogenated vegetable oils may act as controlled release agents.

In one embodiment, the pharmaceutical composition comprises, or consists of, a solid phase mixture consisting of API and non-basic excipients which comprise a cellulosic excipient, e.g. selected from microcrystalline cellulose, hypromellose, ethylcellulose and combinations thereof. In another embodiment, the pharmaceutical composition comprises, or consists of, a solid phase mixture consisting of API and non-basic excipients which comprise a controlled release material, e.g. a non-basic hydrogel-former such as, for example, hypromellose. The solid phase mixture may have at least one coating.

An embodiment of the invention therefore comprises a solid phase mixture, which may be in the form of a tablet, and which consists of a compound of formula A1 or A2 in admixture with: lactose (e.g. as lactose monohydrate); microcrystalline cellulose; a polymer selected from homopolymers of cross-linked N-vinyl-2-pyrrolidone (crospovidone), hypromelloses, and ethyl cellulose; waxes, colloidal silicon dioxide; and a lubricant selected from stearic acid, hydrogenated vegetable oil, mineral oil, polyethylene glycol (e.g. polyethylene glycol 4000-6000), gyceryl palmitostearate and glyceryl behenate, and combinations of the aforesaid lubricant compounds. For example, such an embodiment may comprise a solid phase mixture, which may be in the form of a tablet, and which consists of a compound of formula A1 or A2 in admixture with: lactose (e.g. as lactose monohydrate); microcrystalline cellulose; a polymer selected from homopolymers of cross-linked N-vinyl-2-pyrrolidone (crospovidone) and hypromelloses; colloidal silicon dioxide; and a lubricant selected from hydrogenated vegetable oil, mineral oil, polyethylene glycol (e.g. polyethylene glycol 4000-6000), gyceryl palmitostearate and glyceryl behenate, and combinations of the aforesaid lubricant compounds. In embodiments, a single lubricant is present in the solid phase mixture, particularly glyceryl behenate.

Particle Size

It will be recalled that an aspect of the invention is in part predicated on a finding that the stability in a solid phase composition, particularly a tablet, of an active compound as disclosed above, namely the hemifumarate salt of 1-{4-[1-(4-cyclohexyl-3-trifluoromethyl-benzyloxyimino)-ethyl]-2-ethyl-benzyl}-azetidine-3-carboxylic acid, may be improved by the active compound being in a relatively large particle size but, in most instances, a particle size not so large that the composition fails to comply with the USP, EP and JP harmonised content uniformity requirement, e.g. as in force on 1 Jan. 2011.

It will be appreciated that the hemifumarate salt of 1-{4-[1-(4-cyclohexyl-3-trifluoromethyl-benzyloxyimino)-ethyl]-2-ethyl-benzyl}-azetidine-3-carboxylic acid is a representative of the compounds of formula A1 or A2 as described above and that the just-mentioned measures relating to particle size may therefore be beneficially applied to any such compound as an active pharmaceutical ingredient (API) of a composition. The invention therefore provides a solid phase formulation, particularly a tablet, comprising a compound of formula A1 or A2 in a relatively large particle size, e.g. an X90 diameter of at least 8 µm and often of 10 µm or more, for example 20 µm or 25 µm or more, optionally of 100 µm or more and further optionally of 150 µm or more. The particle size (X90 diameter) may be up to 300 µm, e.g. up to 250 µm, and optionally up to 200 µm (e.g. up to 195 µm). In some embodiments, the X90 diameter is of from 10 µm to 300 µm, e.g. 10 µm to 250 µm or 10 µm to 200 µm. Also included are embodiments in which the particle size (X90 diameter) is from 25 µm to 300 µm, e.g. 25 µm to 250 µm or 25 µm to 200 µm. Further included are embodiments in which the X90 diameter is from 100 µm to 300 µm, e.g. 100 µm to 250 µm or 100 µm to 200 µm. In a particular embodiment, the X90 particle diameter is at least 10 µm and is less than 191 µm, e.g. less than 180 µm, less than 170 µm, less than 160 µm, less than 150 µm, less than 140 µm or less than 130 µm, e.g. no more than 125 µm, such as no more than 121 µm; in a sub-embodiment, the X90 particle diameter is at least 25 µm and is less than 191 µm, e.g. less than 180 µm, less than 170 µm, less than 160 µm, less than 150 µm, less than 140 µm or less than 130 µm, e.g. no more than 125 µm, such as no more than 121 µm. In some instances the X90 particle diameter is at least 10 µm or 25 µm but no more than 100 µm, e.g. is no more than 90 µm, no more than 80 µm, no more than 70 µm, no more than 60 µm, no more than 50 µm or no more than 40 µm, for example is no more than 30 µm. In other embodiments, the X90 particle diameter is from 121 µm to 191 µm. In another embodiment, the X90 particle diameter is from 11 µm to 29 µm.

An aspect of the invention is in part predicated on a finding that, in the case of an API of formula A1 or A2, API particles of the sizes mentioned herein of at least 8 µm may be formulated into tablets which have a tablet content uniformity which fulfills the requirement of the USP, EP and JP harmonised content uniformity requirement, in particular as in force on 1 Jan. 2011. The pharmaceutical compositions of the present invention may fulfil, and desirably do fulfill, the USP, EP and JP harmonised content uniformity requirement (refer to chapter 2.9.40. Uniformity of dosage unit in the EP). A maximum particle size which enables the requirement to be met cannot be stipulated because the maximum possible particles size varies with the drug content of the dosage unit. For example, in the case of a tablet containing 0.25 mg of an API (equivalent base weight), API particles having an X90 diameter of 121 µm complied with the harmonised content uniformity requirement whereas API particles having an X90 diameter of 191 µm failed to comply. In contrast, in the case of a tablet containing 5 mg (equivalent base weight), of an API, API particles having an X90 diameter of up to 191 µm complied with the harmonised content uniformity requirement. A maximum particle size which enables any particular tablet composition to meet the harmonised content uniformity requirement may be determined empirically.

The particle size distribution (by volume) may be measured using a laser diffraction sizing instrument, for example the Sympatec Helos device (available from Sympactec GmbH, Germany) using the Cuvette dispersion device. The $X_{90}$ diameter is the spherical diameter corresponding to the $X_{90}$ volume.

To make the measurement, a stock dispersion may be prepared by mixing the drug substance with a dispersing aid (e.g Octastat 5000 (Octel corp)) using a vortex until a smooth and homogeneous paste is formed. The paste may then be diluted and mixed to a final volume of 3 to 6 ml using white spirit. The optical concentration of the final solution should remain below 5%. The percent values are calculated from the mean cumulative volume size curve by the software of the Sympatec instrument. X90 mean 90% of the particle size population is below the specified value in volume.

Additional confirmatory information on particle size may be obtained using SEM (scanning electron microscopy).

Content uniformity testing is used to test the active content within individual units post-manufacturing (such as the content of active agents within individual tablets after compression).

Content uniformity is influenced by the particle size of the drug substances. Median particle size is denoted by $X_m$, where m is a percentage of the particle size distribution.

The invention includes the following embodiments (optionally in combination with the features of other embodiments disclosed herein):

1) a solid phase pharmaceutical composition in unit dosage form which comprises one or more pharmaceutically acceptable excipients, in particular non-basic excipients, and an API as described herein and which complies with the US Pharmacopeia, European Pharmacopeia and Japanese Pharmacopeia harmonised content uniformity requirements as in force on 1 Jan. 2011;

2) a tablet which comprises one or more pharmaceutically acceptable excipients, in particular non-basic excipients, and an API as described herein in an amount of from 4 mg to 6 mg API (equivalent base weight), the API being as particles have an X90 diameter of at least 100 μm but no more than 300 μm, e.g. from 100 μm to 250 μm, from 100 μm to 200 μm, from 100 μm to 190 μm, from 100 μm to 180 μm, from 100 μm to 170 μm, from 100 μm to 160 μm or from 100 μm to 150 μm;

3) a tablet which comprises one or more pharmaceutically acceptable excipients, in particular non-basic excipients, and an API as described herein in an amount of from 0.2 mg to 1 mg API (equivalent base weight), the API being as particles have an X90 diameter of at least 10 μm but no more than 100 μm, e.g. 10 μm to 90 μm, 10 μm to 80 μm, 10 μm to 70 μm, 10 μm to 60 μm, 10 μm to 50 μm, 10 μm to 40 μm or 10 μm to 30 μm.

An aspect of the invention resides in compounds of formula A1 or A2 when in particulate form having an X90 diameter as disclosed herein, as well as products or compositions of matter comprising such particulate compounds.

Crystallinity

The invention is in part also predicated on a finding that the stability in a solid phase formulation, particularly a tablet, of an active compound as disclosed above, namely the hemifumarate salt of 1-{4-[1-(4-cyclohexyl-3-trifluoromethyl-benzyloxyimino)-ethyl]-2-ethyl-benzyl}-azetidine-3-carboxylic acid, may be enhanced by the active compound being in particles of relatively high crystallinity, e.g. a crystallinity of 80% or more, for example 85% or more and optionally of 90% or more.

It will be appreciated that the above salt of 1-{4-[1-(4-cyclohexyl-3-trifluoromethyl-benzyloxyimino)-ethyl]-2-ethyl-benzyl}-azetidine-3-carboxylic acid is a representative of the compounds of formula A1 or A2 as described above and that the just-mentioned measures may therefore be beneficially applied to any such compound as an active pharmaceutical ingredient (API) of a composition. The invention therefore provides a solid phase formulation, particularly a tablet, comprising a compound of formula A1 or A2 in a crystallinity of 80% or more, for example 85% or more and optionally of 90% or more.

An aspect of the invention resides in compounds of formula A1 or A2 when having a crystallinity of 80% or more, for example 85% or more and optionally of 90% or more, as well as products or compositions of matter comprising compounds having such crystallinity.

Conveniently, a crystallinity of 80% or more may be attained by a compound of formula A1 or A2 being as particles having an X90 diameter of 10 μm or more and particularly 11 μm or more, for example 20 μm or 25 μm or more, optionally of 100 μm or more and further optionally of 150 μm or more. The X90 diameter may be as previously described herein under the heading "Particle Size".

Crystallinity may be measured using any suitable means, for example using X-ray powder diffraction (XRPD), for example using a Bruker D8 device.

It will be appreciated that solid phase compositions, e.g. tablets, may advantageously combine the features of particle size and/or crystallinity disclosed herein with the feature of not exposing the API to a basic compound.

Methods for Making the Pharmaceutical Compositions

Compositions of the invention may suitably be made by combining the components as dry powders, for example tablets may be made by dry granulating the components of the tablet mix and optionally applying a film coating, for example a moisture barrier film, to the compressed tablet.

API particles can be prepared by suitable milling techniques, e.g. those well known in the art such as, for example, wet-jet milling, pin-milling, and wet-ball milling Where the API particles are derived from coarse API particle crystals, the coarse crystals may be obtained using any suitable methodology. For example any of the methodologies set out in WO2010/071794, WO2010/080455 or WO2010/080409.

Of interest in the invention are the following numbered paragraphs.

1. A solid phase pharmaceutical composition comprising one or more pharmaceutically acceptable excipients and an active pharmaceutical ingredient ("API") which is a compound of formula A1 or A2 or a pharmacologically acceptable salt, solvate or hydrate thereof, wherein the API is not exposed to a basic compound:

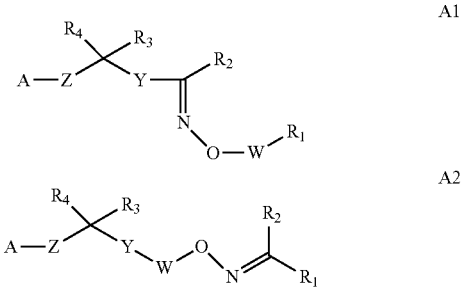

wherein
A is $COOR_5$, $OPO(OR_5)_2$, $PO(OR_5)_2$, $SO_2OR_5$, $POR_5OR_5$ or 1H-tetrazol-5-yl, $R_5$ being H or an ester-forming group;
W is a bond, $C_{1-3}$alkylene or $C_{2-3}$alkenylene;
Y is $C_{6-10}$aryl or $C_{3-9}$heteroaryl, optionally substituted by 1 to 3 radicals selected from halogen, $NO_2$, $C_{1-6}$alkyl, $C_{1-6}$alkoxy; halo-substituted $C_{1-6}$alkyl and halo-substituted $C_{1-6}$alkoxy;

Z is chosen from:

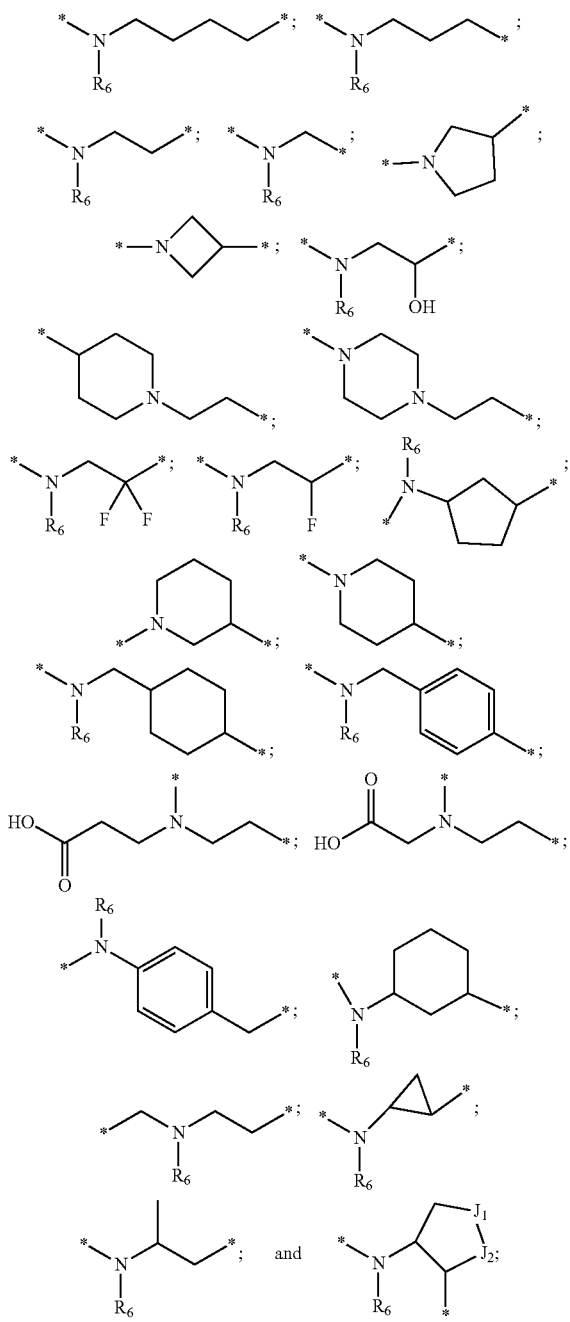

wherein the asterisks of Z indicate the point of attachment between —C(R$_3$)(R$_4$)— and A of Formula Ia or Ib, respectively; R$_5$ is chosen from hydrogen and C$_{1-6}$alkyl; and J$_1$ and J$_2$ are independently methylene or a heteroatom chosen from S, O and NR$_5$; wherein R$_5$ is chosen from hydrogen and C$_{1-6}$alkyl; and any alkylene of Z can be further substituted by one to three radicals chosen from halo, hydroxy, C$_{1-6}$alkyl; or R$_6$ can be attached to a carbon atom of Y to form a 5-7 member ring;

R$_1$ is C$_{6-10}$aryl or C$_{3-9}$heteroaryl, optionally substituted by C$_{1-6}$alkyl, C$_{6-10}$aryl, C$_{6-10}$arylC$_{1-4}$alkyl, C$_{3-9}$heteroaryl, C$_{3-9}$heteroarylC$_{1-4}$alkyl, C$_{3-8}$cycloalkyl, C$_{3-8}$cycloalkylC$_{1-4}$alkyl, C$_{3-8}$heterocycloalkyl or C$_{3-8}$heterocycloalkylC$_{1-4}$alkyl; wherein any aryl, heteroaryl, cycloalkyl or heterocycloalkyl of R$_1$ may be substituted by 1 to 5 groups selected from halogen, C$_{1-6}$alkyl, C$_{1-6}$alkoxy and halo substituted-C$_{1-6}$alkyl or —C$_{1-6}$alkoxy;

R$_2$ is H, C$_{1-6}$alkyl, halo substituted C$_{1-6}$alkyl, C$_{2-6}$alkenyl or C$_{2-6}$alkynyl; and each of R$_3$ or R$_4$, independently, is H, halogen, OH, C$_{1-6}$alkyl, C$_{1-6}$alkoxy or halo substituted C$_{1-6}$alkyl or C$_{1-6}$alkoxy.

2. A composition of numbered paragraph 1 wherein A is COOH.

3. A composition of numbered paragraph 1 or 2 wherein the compound is of formula A1.

4. A composition of numbered paragraph 3 wherein:
W is C$_1$, C$_2$ or C$_3$ alkylene;
Y is a phenyl group optionally substituted by 1, 2 or 3 radicals selected from halogen, NO$_2$, C$_{1-6}$alkyl, C$_{1-6}$alkoxy; halo-substituted C$_{1-6}$alkyl and halo-substituted C$_{1-6}$alkoxy; and
R$_1$ is phenyl substituted by C$_3$-C$_8$ cycloalkyl, wherein phenyl and cyclohexyl are each independently optionally substituted by 1 or 2 substituents selected from halogen, C$_{1-6}$alkyl, C$_{1-6}$alkoxy and halo substituted- C$_{1-6}$ alkyl or —C$_{1-6}$alkoxy.

5. A composition of numbered paragraph 1 wherein the API is 1-{4-[1-(4-cyclohexyl-3-trifluoromethyl-benzyloxy-imino)-ethyl]-2-ethyl-benzyl}-azetidine-3-carboxylic acid or a pharmaceutically acceptable salt.

6. A composition of numbered paragraph 1 wherein the API is 1-{4-[1-(4-cyclohexyl-3-trifluoromethyl-benzyloxy-imino)-ethyl]-2-ethyl-benzyl}-azetidine-3-carboxylic acid or a hemifumarate salt thereof.

7. A composition of any preceding numbered paragraph wherein the API is in a mixture of materials which is free of basic compounds.

8. A composition of any preceding numbered paragraph which is a tablet.

9. A composition of numbered paragraph 8 wherein the tablet is coated with a moisture barrier.

10. A composition of numbered paragraph 8 or 9 wherein the tablet comprises a solid phase mixture which consists of the API in admixture with: lactose; microcrystalline cellulose; a polymer selected from homopolymers of cross-linked N-vinyl-2-pyrrolidone (crospovidone) and hypromelloses; colloidal silicon dioxide; and a lubricant selected from hydrogenated vegetable oil, mineral oil, polyethylene glycol, gyceryl palmitostearate and glyceryl behenate.

11. A solid phase pharmaceutical composition comprising one or more pharmaceutically acceptable excipients and an active pharmaceutical ingredient ("API") selected from the compounds as defined in any of numbered paragraphs 1 to 6, wherein the API is in the form of particles having an X90 diameter of at least 8 μm.

12. A composition of numbered paragraph 11 wherein the particles have an X90 diameter of from 10 μm to 300 μm.

13. A composition of numbered paragraph 12 wherein the particles have an X90 diameter of at least 10 μm but no more than 100 μm.

14. A composition of numbered paragraph 12 wherein the particles have an X90 diameter of at least 100 μm but no more than 250 μm.

15. A composition of any of numbered paragraphs 11 to 14 which is in unit dosage form and complies with the US Pharmacopeia, European Pharmacopeia and Japanese Pharmacopeia harmonised content uniformity requirements as in force on 1 Jan. 2011.

16. A composition of numbered paragraph 15 which is in the form of a tablet containing from 4 mg to 6 mg API (equivalent base weight) and particles have an X90 diameter of at least 100 μm but no more than 200 μm.

17. A composition of numbered paragraph 15 which is in the form of a tablet containing from 0.2 mg to 1 mg API (equivalent base weight) and particles have an X90 diameter of at least 10 μm but no more than 50 μm.

18. A composition of any of numbered paragraphs 11 to 17 which further includes the features of any one of, or any combination permitted by dependency of, of numbered paragraphs 1 to 10.

19. A solid phase pharmaceutical composition comprising one or more pharmaceutically acceptable excipients and an active pharmaceutical ingredient ("API") selected from the compounds as defined in any of numbered paragraphs 1 to 6, wherein the API has a crystallinity of 80% or more.

20. A composition of numbered paragraph 19 wherein the API has a crystallinity of 85% or more.

21. A composition of numbered paragraph 19 or 20 which is a tablet.

22. A composition of any of numbered paragraphs 18 to 21 which further includes the features of any one of, or any combination permitted by dependency of, of numbered paragraphs 1 to 10 and 11 to 17.

23. A tablet comprising a compressed mixture consisting of 1-{4-[1-(4-cyclohexyl-3-trifluoromethyl-benzyloxyimino)-ethyl]-2-ethyl-benzyl}-azetidine-3-carboxylic acid or a pharmaceutically acceptable salt thereof and one or more non-basic excipients, the 1-{4-[1-(4-cyclohexyl-3-trifluoromethyl-benzyloxyimino)-ethyl]-2-ethyl-benzyl}-azetidine-3-carboxylic acid or pharmaceutically acceptable salt being in the form of particles having an X90 diameter of from 10 μm to 200 μm.

24. A tablet of numbered paragraph 23, wherein the pharmaceutically acceptable salt is a hemifumarate salt.

25. A tablet of numbered paragraph 23 or 24 wherein said particles are at least 80% crystalline.

26. A tablet of numbered paragraph 23, 24 or 25 wherein the compressed mixture includes a desiccant and is coated with a moisture barrier.

Specific tablet embodiments of the formulations of the present invention wherein the active agent, 1-{4-[1-(4-cyclohexyl-3-trifluoromethyl-benzyloxyimino)-ethyl]-2-ethyl-benzyl}-azetidine-3-carboxylic acid, is present in amounts of 0.25 mg, 0.5 mg, and 1.0 mg, respectively, are described in the chart below.

Another specific tablet embodiment of the formulations of the present invention wherein the active agent, 1-{4-[1-(4-cyclohexyl-3-trifluoromethyl-benzyloxyimino)-ethyl]-2-ethyl-benzyl}-azetidine-3-carboxylic acid, is present in an amount of 2.0 mg, is described in the chart below.

| Dosage strenght | 2.0 mg | |
| --- | --- | --- |
| Per FCT | mg | % |
| BAF312 | 2.224 | 2.482 |
| Glyceryl behenate | 4.25 | 4.743 |
| Lactose Spray dried | 60.251 | 67.244 |
| Cellulose | 12.75 | 14.230 |
| Polyvinyl Polypyrolidone XL | 5.1 | 5.692 |
| Aerosil | 0.425 | 0.474 |
| Total TAB | 85 | 94.866 |
| Opadry AMB ® | 4.6 | 5.134 |
| total FCT | 89.6 | 100.000 |

EXAMPLES

Example 1

The following Example illustrates the stability of the hemifumarate salt of 1-{4-[1-(4-cyclohexyl-3-trifluoromethyl-benzyloxyimino)-ethyl]-2-ethyl-benzyl}-azetidine-3-carboxylic acid in the presence of various compounds. Mixtures of this API with various compounds were exposed in a sealed vial to conditions of 50° C. temperature and 75% relative humidity for 4 weeks. After 4 weeks, the API degradation and sum of degradation products were assayed. The results are displayed in Table 1.

Assay method: HPLC using agilent 11000 and a Phenomenex Gemini C18 column. UV detection at 260 nm was used. The mobile phase used was a gradient water-acetonitrile containing 0.2% (v/v) formic acid and 10% (v/v) Triethylamine.

The hemifumarate salt of 1-{4-[1-(4-cyclohexyl-3-trifluoromethyl-benzyloxyimino)-ethyl]-2-ethyl-benzyl}-azetidine-3-carboxylic acid is described as "NVS-A" in Table 1.

Table 1

| Mixture | Sum of unknown peaks (%)* | Assay (%)* |
| --- | --- | --- |
| NVS-A alone | 1.86 | 100.2 |
| NVS-A + Lactose (1:1) | 1.74 | 96.5 |

| Dosage strenght | 0.25 mg | | 0.5 mg | | 1.0 mg | |
| --- | --- | --- | --- | --- | --- | --- |
| Per FCT | mg | % | mg | % | mg | % |
| BAF312 | 0.278 | 0.310 | 0.556 | 0.621 | 1.112 | 1.241 |
| Glyceryl behenate | 4.25 | 4.743 | 4.25 | 4.743 | 4.25 | 4.743 |
| Lactose Spray dried | 62.197 | 69.416 | 61.919 | 69.106 | 61.363 | 68.485 |
| Cellulose | 12.75 | 14.230 | 12.75 | 14.230 | 12.75 | 14.230 |
| Polyvinyl Polypyrolidone XL | 5.1 | 5.692 | 5.1 | 5.692 | 5.1 | 5.692 |
| Aerosil | 0.425 | 0.474 | 0.425 | 0.474 | 0.425 | 0.474 |
| Total TAB | 85 | 94.866 | 85 | 94.866 | 85 | 94.866 |
| Opadry AMB ® | 4.6 | 5.134 | 4.6 | 5.134 | 4.6 | 5.134 |
| total FCT | 89.6 | 100.000 | 89.6 | 100.000 | 89.6 | 100.000 |

-continued

| Mixture | Sum of unknown peaks (%)* | Assay (%)* |
|---|---|---|
| NVS-A + Maize Starch (1:1) | 1.82 | 99.4 |
| NVS-A + Microcrystalline Cellulose (1:1) | 1.80 | 99.0 |
| NVS-A + Mannitol (1:1) | 1.80 | 99.2 |
| NVS-A + HPMC (1:1) | 2.45 | 97.7 |
| NVS-A + PVP K30 (1:1) | 2.07 | 99.6 |
| NVS-A + Ac-Di-Sol (1:1) | 1.89 | 99.7 |
| NVS-A + Primojel (1:1) | 4.08 | 100.9 |
| NVS-A + Crospovidone (1:1) | 1.89 | 99.7 |
| NVS-A + Mgstearate (1:0.85) | 0.31 | 98.2 |
| NVS-A + Mg Stearate (1:0.85)* | 3.68 | 90.0 |
| NVS-A + Sodium LaurylSulfate (SLS) + Microcrystalline Cellulose (2:1:1) | 8.54 | 88.3 |
| NVS-A + Gelatin (1:1) | 3.86 | 96.1 |
| NVS-A + Aerosil + Microcrystalline Cellulose (2:1:1) | 1.89 | 99.9 |
| NVS-A + Magnesium Stearate (Mg St) + Microcrystalline Cellulose (2:1:1) | 6.13 | 89.2 |
| NVS-A + Magnesium stearate + Microcrystalline Cellulose (2:1:1 | 10.53 | 80.7 |
| NVS-A + Magnesium stearate + lactose (2:1:1) | 9.31 | 82.2 |
| NVS-A + Calcium stearate + Microcrystalline Cellulose (2:1:1) | 4.55 | 89.8 |
| NVS-A + sodium stearyl fumarate Microcrystalline Cellulose (2:1:1) | 7.52 | 83.1 |
| NVS-A + Sodium bicarbonate + Microcrystalline Cellulose (2:1:1) | 8.48 | 61.8 |
| NVS-A + Tween 80 + Microcrystalline Cellulose (2:1:1) | 2.07 | 100.1 |

*at 50° C./75% RH opened vial/4 weeks

Example 2

The following Example demonstrates the detrimental effect of magnesium stearate on the hemifumarate salt of 1-{4-[1-(4-cyclohexyl-3-trifluoromethyl-benzyloxyimino)-ethyl]-2-ethyl-benzyl}-azetidine-3-carboxylic acid (NVS-A).

A film coated tablet containing NVS-A was developed comprising micronised drug substance, lactose monohydrate, microcrystalline cellulose, crospovidone, colloidal silicon dioxide, and magnesium stearate. A moisture protective Opadry® AMB film coating was applied. Tablet strengths from 0.25 mg to 5 mg (equivalent free base weight) were produced as shown in Table 2 below.

TABLE 2

Composition of the immediate release 0.25 and 5 mg tablet containing magnesium stearate as lubricant.

| Ingredient | Amount (mg) per 0.25 mg tablet | Amount (mg) per 5 mg tablet | Function | Reference to standards |
|---|---|---|---|---|
| Tablet core | | | | |
| NVS-A | 0.278[1] | 5.560[2] | Drug substance | Novartis monograph |
| Lactose monohydrate | 63.897 | 58.615 | Diluent | Ph. Eur./NF |
| Microcrystalline cellulose/ Cellulose microcrystalline | 17.000 | 17.000 | Diluent | Ph. Eur./NF |
| Crospovidone | 2.550 | 2.550 | Disintegrant | Ph. Eur./NF |
| Silica, colloidal anhydrous/ Colloidal silicon dioxide | 0.425 | 0.425 | Gliding agent | Ph. Eur./NF |
| Magnesium stearate | 0.850 | 0.850 | Lubricant | Ph. Eur./NF |
| Core tablet weight | 85.000 | 85.000 | | |
| Coating | | | | |
| Coating premix Opadry AMB white** | 3.400 | 3.400 | Coating agent | |
| Water, purified* | 13.600 | 13.600 | Solvent | Ph.Eur./USP |
| Total film-coated tablet weight | 88.400 | 88.400 | | |
| Tablet core | | | | |

| Coating premix ingredient | Reference to standards |
|---|---|
| Polyvinyl alcohol-part hydrolised | Ph.Eur./USP |
| Titanium dioxide | Ph.Eur./USP |
| Talc | Ph.Eur./USP |
| Lecithin (soya) | NF |
| Xanthan gum | Ph.Eur./NF |

[1]Corresponds to 0.25 mg (e.g. 0.294% w/w) NVS-A base respectively
[2]Corresponds to 5 mg (e.g 5.88% w/w) NVS-A base respectively
* Removed during processing
**The qualitative composition of the coating premix is as follows:

The tablets were only stable for prolonged periods at 2-8° C. At 25° C., the 0.25 mg strength tablet was stable for only 6 months and the 5 mg tablet was stable for only 12 months. Beyond 6 months and 12 months at 25° C. respectively for the 0.25 and 5 mg tablet, the stability data did not fulfill the stability guidance from the International Conference on Harmonisation of Technical Requirements for Registration of Pharmaceuticals for Human Use (ICH).

Example 3

The effect of drug particle size on the content uniformity of a tablet comprising 5 mg (equivalent free base weight) of the hemifumarate salt of 1-{4-[1-(4-cyclohexyl-3-trifluoromethyl-benzyloxyimino)-ethyl]-2-ethyl-benzyl}-azetidine-3-carboxylic acid (NVS-A) was studied.

The $X_{90}$ particle size distribution (by volume) was measured using a laser diffraction sizing instrument [the Sympatec Helos device (available from Sympactec GmbH, Germany) using the Cuvette dispersion device. To make the measurement, a stock dispersion was prepared by mixing the drug substance with a dispersing aid (Octastat 5000 (Octel corp)) using a vortex until a smooth and homogeneous paste was formed. The paste was then diluted and mixed to a final volume of 3 to 6 ml using white spirit. The optical concentration of the final solution were kept below 5%. The percentage values were calculated from the mean cumulative volume size curve by the software of the Sympatec instrument. Additional confirmatory information on particle size was obtained using SEM (scanning electron microscopy).

The finer API material ($X_{90}$<10 μm (4 and 7 μm) was obtained by micronisation using a jet mill [Hosokawa Alpine AFG100] using a pressure in the range from 2 to 5 bars. The material with $X_{90}$ at 11, 29 μm and 121 μm was obtained by milling in this case with a pin mill with the relative tin speed being adjusted from 115, to 75 to 40 m/sec respectively. Finally, the coarser material with $X_{90}$ μm of 191 μm was obtained by sieving on a 457 μm sieve. The results are presented in FIG. 1.

The drug substance particle sizes considered showed reduced impact on the mean content uniformity value and its variability for the 5 mg tablet:

where X90=191 μm, the content uniformity ranged from about 97.3% to about 104.0% where X90=121 μm, the content uniformity ranged from about 92.8% to about 99.7% where X90=29 μm, the content uniformity ranged from about 97.2% to about 102.9% where X90=11 μm, the content uniformity ranged from about 97.3% to 100.1% where X90=7 μm, the content uniformity ranged from about 94.1% to 98.9% where X90=4 μm, the content uniformity ranged from about 93.3% to 99.1%.

This study demonstrated that despite the low tablet strength, micronised drug substance (where X90=4 μm to 7 μm) was not essential to fulfil the USP, EP and JP harmonised content uniformity requirement. This requirement could be achieved when using milled drug substance (where X90=11 μm to 29 μm) and also unexpectedly using the coarse drug substance (where X90=121 μm to 191 μm).

Example 4

The effect of drug particle size on the content uniformity of a tablet comprising 0.25 mg (equivalent free base weight) of the hemifumarate salt of 1-{4-[1-(4-cyclohexyl-3-trifluoromethylbenzyloxyimino)-ethyl]-2-ethyl-benzyl}-azetidine-3-carboxylic acid (NVS-A) was studied. API drug particles were obtained and measured as in Example 3.

Figure 2:
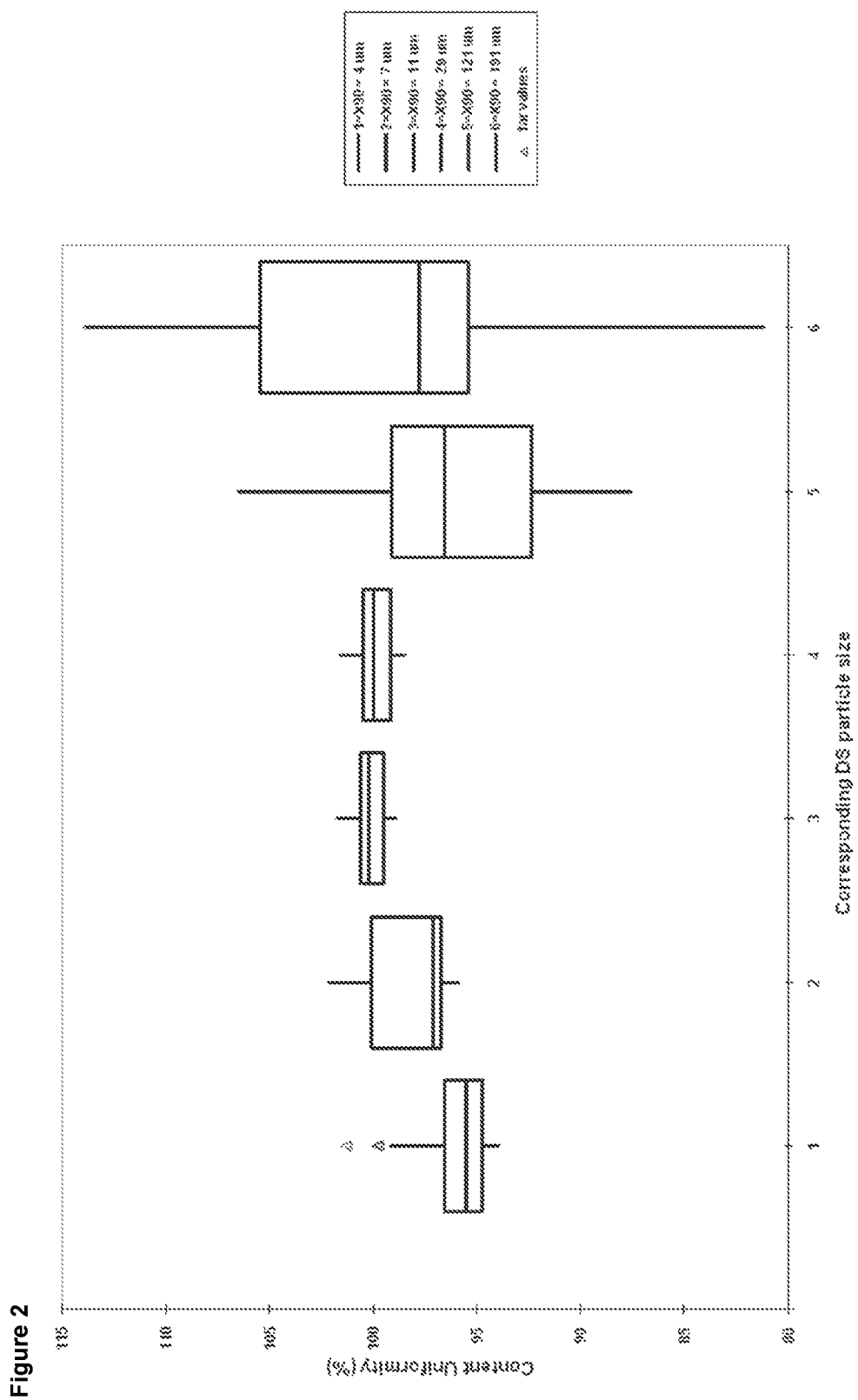
FIG. 2 is a box plot which demonstrates the effect of drug particle size on the content uniformity of a tablet comprising 0.25 mg (equivalent base weight) of the hemifumarate salt of 1-{4-[1-(4-cyclohexyl-3-trifluoromethyl-benzyloxyimino)-ethyl]-2-ethyl-benzyl}-azetidine-3-carboxylic acid.

The results are presented in FIG. 2.

Coarse drug substance with an X90 diameter of 121 μm and 191 μm led to a significant increase in content uniformity variability:

where X90=191 μm, the content uniformity ranged from about 81.2% to about 113.9% where X90=121 μm, the content uniformity ranged from about 87.6% to about 106.5%.

Milled drug substance with an X90 of 11 μm or 29 μm led to a better centered mean content uniformity and a slightly lower content variability than the one observed with the micronised drug substance (X90=4 and 7 μm):

where X90=29 μm, the content uniformity ranged from about 98.5% to about 101.6% where X90=11 μm, the content uniformity ranged from about 98.9% to about 101.8% where X90=7 μm, the content uniformity ranged from about 95.9% to about 102.2% where X90=4 μm, the content uniformity ranged from about 94.0% to about 101.3%.

This example demonstrates that despite the low tablet strength, micronised drug substance (where X90=4 μm to 7 μm) is not essential to fulfil the USP, EP and JP harmonised content uniformity requirement. This requirement can unexpectedly be achieved when using milled drug substance (where X90=11 μm to 29 μm). The upper limit that achieved the USP, EP and JP harmonised content uniformity requirement was a 0.25 mg tablet with a particle size characterised by a X90=121 μm.

Example 5

The following example compares the sum of degradation products of four different compositions, each comprising 0.25 mg (equivalent free base weight) of the hemifumarate salt of 1-{4-[1-(4-cyclohexyl-3-trifluoromethyl-benzyloxyimino)-ethyl]-2-ethyl-benzyl}-azetidine-3-carboxylic acid (NVS-A) mixed with a lubricant. API drug particles were obtained and measured as in Example 3. The lubricants and the particle sizes of each composition are as follows. The table below summarises the difference in composition between the tablets made with magnesium stearate and glyceryl behenate as lubricant. It should be noted that the tablet made with glyceryl behenate and with the different drug substance particle size were not coated with the moisture protective film coated opadry AMB in order to better demonstrate the stability benefit. API drug particles were obtained and measured as in

TABLE 3

Composition of the immediate release 0.25 mg tablet (equivalent free base weight) containing magnesium stearate and glyceryl behenate as lubricant.

| Ingredient | Amount (mg) per 0.25 mg tablet with magnesium sterate as lubricant | Amount (mg) per 0.25 mg tablet with glyceryl behenate as lubricant | Function | Reference to standards |
|---|---|---|---|---|
| Tablet core | | | | |
| NVS-A | 0.278[1] | 0.278[1] | Drug substance | Novartis monograph |
| Lactose monohydrate | 63.897 | 58.797 | Diluent | Ph. Eur./NF |
| Microcrystalline cellulose/ Cellulose microcrystalline | 17.000 | 17.000 | Diluent | Ph. Eur./NF |
| Crospovidone | 2.550 | 2.550 | Disintegrant | Ph. Eur./NF |
| Silica, colloidal anhydrous/ Colloidal silicon dioxide | 0.425 | 0.425 | Gliding agent | Ph. Eur./NF |
| Magnesium stearate | 0.850 | 0 | Lubricant | Ph. Eur./NF |
| Glyceryl behenate | 0 | 5.950 | Lubricant | |
| Core tablet weight | 85.000 | 85.000 | | |
| Coating | | | | |
| Coating premix Opadry AMB white** | 3.400 | 0 | Coating agent | |
| Water, purified* | 13.600 | 0 | Solvent | Ph.Eur./USP |
| Total film-coated tablet weight | 88.400 | Not applicable | | |

| Coating premix ingredient | Reference to standards |
|---|---|
| Polyvinyl alcohol-part hydrolised | Ph.Eur./USP |
| Titanium dioxide | Ph.Eur./USP |
| Talc | Ph.Eur./USP |
| Lecithin (soya) | NF |
| Xanthan gum | Ph.Eur./NF |

[1]Corresponds to 0.25 mg (e.g. 0.294% w/w) NVS-A base respectively
*Removed during processing
**The qualitative composition of the coating premix is as follows:

1. Magnesium stearate, micronised drug substance X90<8 μm.
2. Glyceryl behenate, micronised drug substance X90<8 μm.
3. Glyceryl behenate, milled drug substance X90=11 μm.
4. Glyceryl behenate, milled drug substance X90=29 μm.

Figure 3:
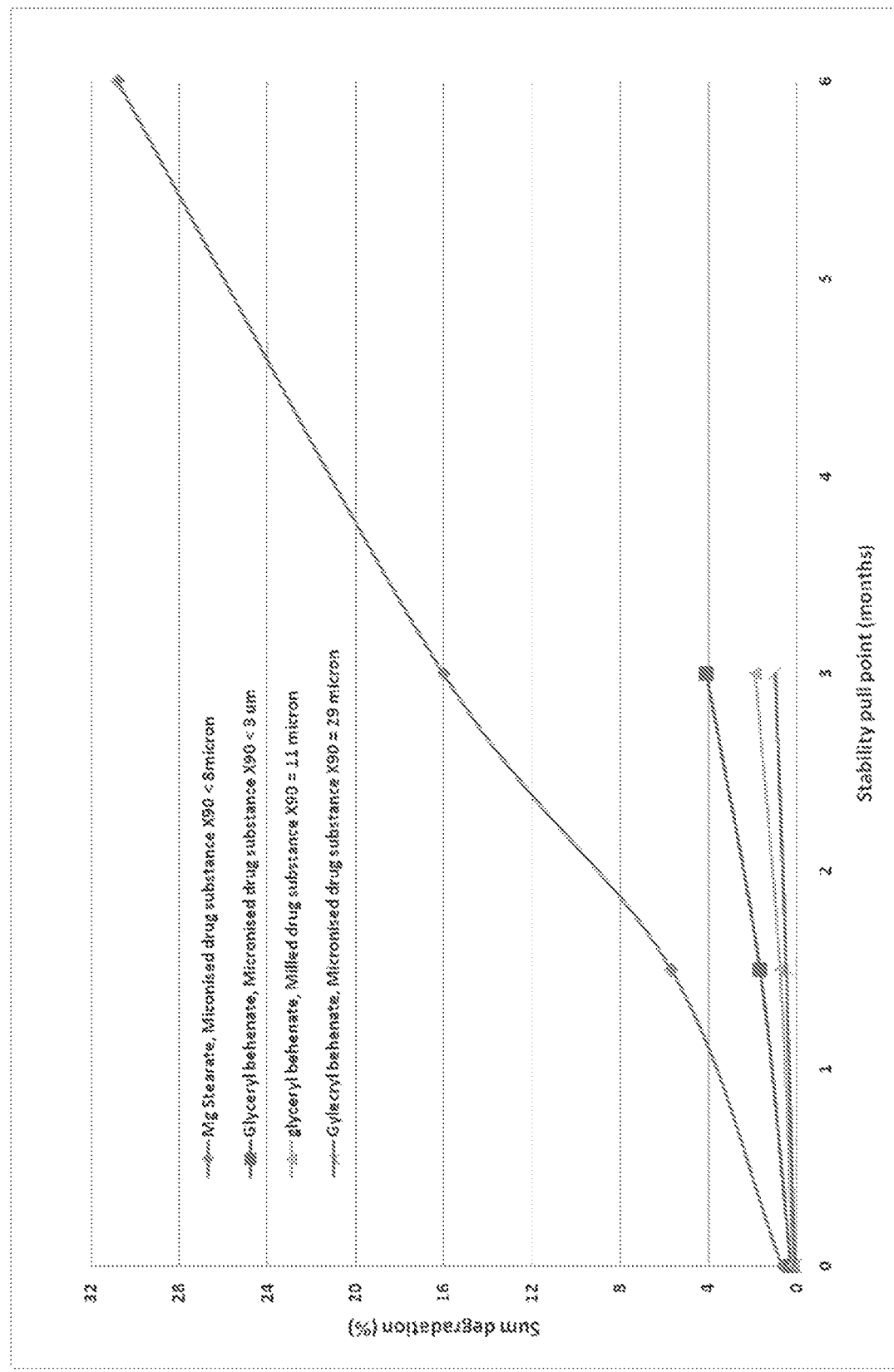
FIG. 3 is a line graph which compares the sum of degradation products of four different compositions, each comprising 0.25 mg (equivalent base weight) of the hemifumarate salt of 1-{4-[1-(4-cyclohexyl-3-trifluoromethyl-benzyloxyimino)-ethyl]-2-ethyl-benzyl}-azetidine-3-carboxylic acid mixed with a lubricant.

Each of the 4 compositions were stored at 40° C. in 75% relative humidity. The evolution of degradation product for each composition was followed over a period of six months. The results are shown in FIG. 3.

Composition 1 exhibited around 16% degradation product after 3 months of storage.

Composition 2 exhibited around 4% degradation product after 3 months of storage.

Composition 3 exhibited around 2% degradation product after 3 months of storage.

Composition 4 exhibited around 1% degradation product after 3 months of storage.

These results demonstrate that replacing magnesium stearate with glyceryl behenate reduces the sum of degradation product. Furthermore, changing the drug substance quality from micronized (less than 80% crystallinity) to milled (greater than 80% crystallinity) also reduces the sum of degradation product.

The invention claimed is:

1. A solid phase pharmaceutical composition comprising one or more pharmaceutically acceptable non-basic excipients and 1-{4-[1-(4-cyclohexyl-3-trifluoromethyl-benzyloxyimino)-ethyl]-2-ethyl-benzyl}-azetidine-3-carboxylic acid or a pharmacologically acceptable salt thereof, wherein at least one of the one or more pharmaceutically acceptable non-basic excipients is glyceryl behenate, and wherein the solid phase pharmaceutical composition does not comprise magnesium stearate.

2. The composition of claim 1, wherein the composition comprises 1-{4-[1-(4-cyclohexyl-3-trifluoromethyl-benzyloxyimino)-ethyl]-2-ethyl-benzyl}-azetidine-3-carboxylic acid and fumaric acid.

3. The composition of claim 1, wherein the composition comprises 1-{4-[1-(4-cyclohexyl-3-trifluoromethyl-benzyloxyimino)-ethyl]-2-ethyl-benzyl}-azetidine-3-carboxylic acid and fumaric acid in the form of particles having an X90 diameter of 8 μm to 121 μm, wherein 0.25 mg of 1-{4-[1-(4-cyclohexyl-3-trifluoromethyl-benzoyloxyimino)-ethyl]-2-ethyl-benzyl}-azetidine-3-carboxylic acid is present in the composition.

4. The composition of claim 3, wherein the particles have an X90 diameter of 8 μm to 40 μm.

5. The composition of claim 1, which is in unit dosage form and complies with the US Pharmacopeia, European Pharmacopeia and Japanese Pharmacopeia harmonized content uniformity requirements as in force on 1 Jan. 2011.

6. A tablet comprising a compressed mixture comprising 1-{4-[1-(4-cyclohexyl-3-trifluoromethyl-benzyloxyimino)-ethyl]-2-ethyl-benzyl}-azetidine-3-carboxylic acid and one or more non-basic excipients, wherein at least one of the one or more pharmaceutically acceptable non-basic excipients is glyceryl behenate, and wherein the tablet does not comprise magnesium stearate.

7. The tablet of claim 6, wherein the compressed mixture comprises 1-{4-[1-(4-cyclohexyl-3-trifluoromethyl-benzyloxyimino)-ethyl]-2-ethyl-benzyl}-azetidine-3-carboxylic acid and fumaric acid.

8. The tablet of claim 6, wherein the tablet includes colloidal silica.

9. The tablet of claim 8, wherein the one or more non-basic excipients are chosen from binders, disintegrants, glidants, fillers, diluents, and sorbents.

10. The composition of claim 1, wherein the one or more pharmaceutically acceptable non-basic excipients are chosen from binders, disintegrants, glidants, fillers, diluents, and sorbents.

11. The tablet of claim 9, wherein the compressed mixture comprises 1-{4-[1-(4-cyclohexyl-3-trifluoromethyl-benzyloxyimino)-ethyl]-2-ethyl-benzyl}-azetidine-3-carboxylic acid and fumaric acid in the form of particles having an X90 diameter of 8 μm to 121 μm, wherein 0.25 mg of 1-{4-[1-(4-cyclohexyl-3-trifluoromethyl-benzoyloxyimino)-ethyl]-2-ethyl-benzyl}-azetidine-3-carboxylic acid is present in the tablet.

12. The tablet of claim 11, wherein the particles have an X90 diameter of 8 μm to 40 μm.

* * * * *